United States Patent
Oyama

(10) Patent No.: US 6,686,845 B2
(45) Date of Patent: Feb. 3, 2004

(54) DRIVER'S AROUSAL LEVEL ESTIMATING APPARATUS FOR VEHICLE AND METHOD OF ESTIMATING AROUSAL LEVEL

(75) Inventor: Hajime Oyama, Tokyo (JP)

(73) Assignee: Fuji Jukogyo Kabushiki Kaisha, Tokyo (JP)

(*) Notice: Subject to any disclaimer, the term of this patent is extended or adjusted under 35 U.S.C. 154(b) by 43 days.

(21) Appl. No.: 09/988,680

(22) Filed: Nov. 20, 2001

(65) Prior Publication Data
US 2002/0097160 A1 Jul. 25, 2002

(30) Foreign Application Priority Data
Nov. 24, 2000 (JP) .......................... 2000-357410

(51) Int. Cl.$^7$ .............................. G08B 23/00
(52) U.S. Cl. .................. 340/575; 340/576; 340/438; 340/439; 340/441; 340/905
(58) Field of Search ................. 340/575, 576, 340/439, 438, 441, 905; 180/272; 128/898, 200.24

(56) References Cited

U.S. PATENT DOCUMENTS

| | | | |
|---|---|---|---|
| 4,928,090 A | * | 5/1990 | Yoshimi et al. ............. 340/575 |
| 5,488,353 A | * | 1/1996 | Kawakami et al. .......... 340/576 |
| 5,815,070 A | * | 9/1998 | Yoshikawa ................... 340/576 |
| 6,335,689 B1 | * | 1/2002 | Mine ........................... 340/576 |

FOREIGN PATENT DOCUMENTS

| | | |
|---|---|---|
| JP | 5-58192 | 3/1993 |
| JP | 9-99756 | 4/1997 |
| JP | 2000-185575 | 7/2000 |

* cited by examiner

*Primary Examiner*—Jeffery Hofsass
*Assistant Examiner*—Hung Nguyen
(74) *Attorney, Agent, or Firm*—McGinn & Gibb, PLLC

(57) ABSTRACT

A driver's arousal level estimating apparatus for a vehicle includes a Fast Fourier Transformation (FFT) signal processing section for obtaining respective frequency component powers by applying a frequency conversion to displacement quantities successively detected of the vehicle, an evaluation value calculating section for calculating an evaluation value from a ratio of an average value of the respective calculated frequency powers and a maximum value of frequency component powers in a specified frequency domain containing a predetermined lateral fluctuation frequency characteristic of a lowered arousal level, and a judging section for judging a driver's arousal level based on the evaluation value.

25 Claims, 6 Drawing Sheets

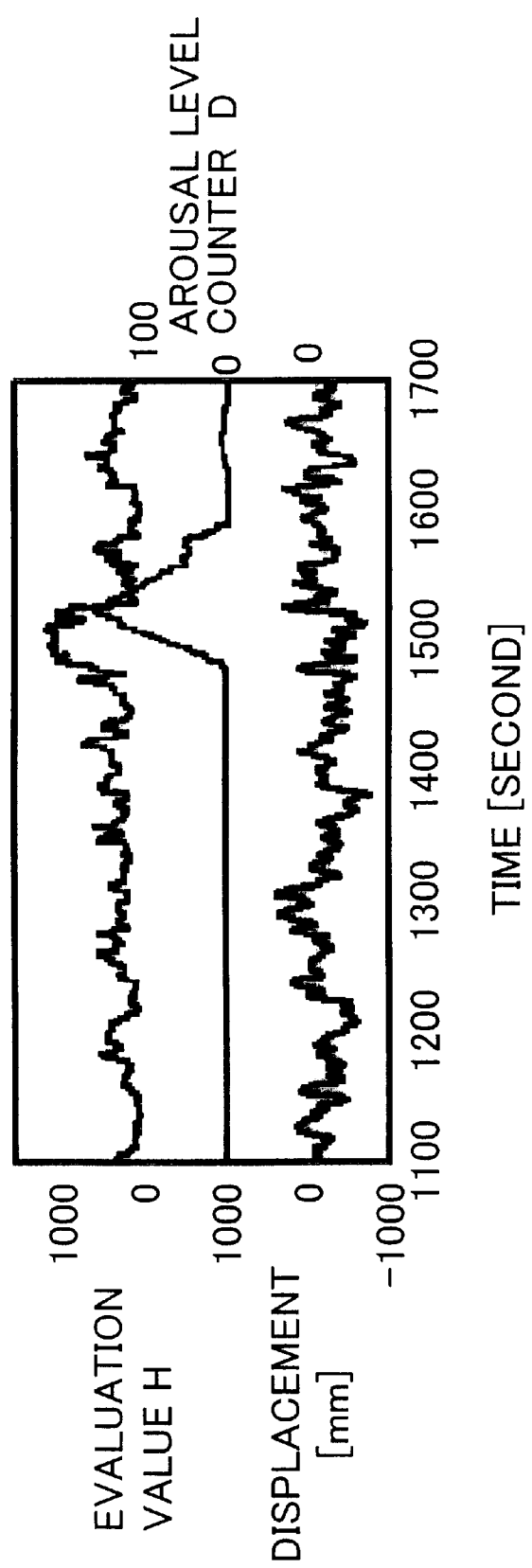

DRIVER'S AROUSAL LEVEL ESTIMATING APPARATUS FOR VEHICLE AND METHOD OF ESTIMATING AROUSAL LEVEL

BACKGROUND OF THE INVENTION

1. Field of the Invention

The present invention relates to an apparatus and method of estimating an arousal level of a vehicle driver by particularly monitoring lateral displacements of a vehicle.

2. Description of Background Arts

A technology for preventing car accidents caused by the decline of driver's arousal level is one of most important developmental subjects of today from the view point of vehicle safety. In recent years, studies for detecting drowsiness or arousal level of vehicle drivers, developments of techniques for warning them against falling into drowsy state are vigorously undertaken. When driver's arousal level descends, especially when a vehicle travels at high speeds, serious accidents may happen. Even if he or she does not fall into such drowsy state, drowsiness induces him or her to an absent-minded state which hinders a quick action for averting accidents, this also leading to accidents.

Japanese Patent Application Laid-open No. Toku-Kai-Hei 5-58192 discloses a technique in which so-called "dozing at the wheel" is detected based on low frequency components in displacement quantity of a vehicle. In this disclosure, displacement quantities such as steering angle, lateral displacement of a vehicle and the like are monitored consecutively and low frequency components in frequency spectrum of the displacement quantity are extracted. On the other hand, low frequency components in frequency spectrum of displacement quantity at normal operations are memorized as sample data beforehand. Then, the low frequency components after a specified time elapses from the start of the vehicle are compared with those sample data. If a difference between the low frequency components and the sample data exceeds a predetermined value, it is judged that the driver dozes at the wheel.

However, the sample data which are used for the judgment reference are ones collected under a certain traveling condition (weather, road surface conditions, time, degree of traffic jams, vehicle speed and others). If the traveling condition changes, the judgment whether or not the driver is in a dozing state is accompanied by errors. That is, this background art has a problem that, when the traveling condition changes largely, it is difficult to obtain a correct judgment as to whether or not the driver is in a dozing state.

The applicant of the present invention has already proposed a method of estimating arousal level to solve such a problem in Japanese Patent Application Laid-open No. Toku-Kai 2000-185575. According to the technique disclosed in this publication, quantities of displacement in a widthwise direction of the vehicle are detected consecutively and respective frequency component powers are obtained by applying frequency conversion to these quantities of displacement. Next, the frequency domain is divided into a low frequency domain and a high frequency domain and an integration A1 of the frequency components powers in the low frequency domain and an integration A2 of the frequency components powers in the high frequency domain are obtained respectively. Then, evaluation values are calculated using these integrations A1, A2 and an arousal level of a vehicle driver is judged based on the evaluation values.

SUMMARY OF THE INVENTION

It is an object of the present invention to provide an arousal level estimating apparatus capable of making an accurate judgment of driver's arousal level.

To achieve the object, an arousal level estimating apparatus comprises a power calculating means for calculating a frequency component power by applying a frequency conversion method to a lateral displacement quantity detected successively, a first evaluation value calculating means for calculating a first evaluation value based on a sum of the frequency component power calculated by the power calculating means, a second evaluation value calculating means for calculating a maximum value of frequency component power in a specified frequency domain including a fluctuation frequency as a second evaluation value, an evaluation value calculating means for calculating an evaluation value from a ratio of the first evaluation value and the second evaluation value and a judging means for judging a driver's arousal level based on the evaluation value.

BRIEF DESCRIPTION OF DRAWINGS

FIG. 7 is a diagram showing actual measuring results in traveling on a high way.

DESCRIPTION OF PREFERRED EMBODIMENTS

Figure 1:
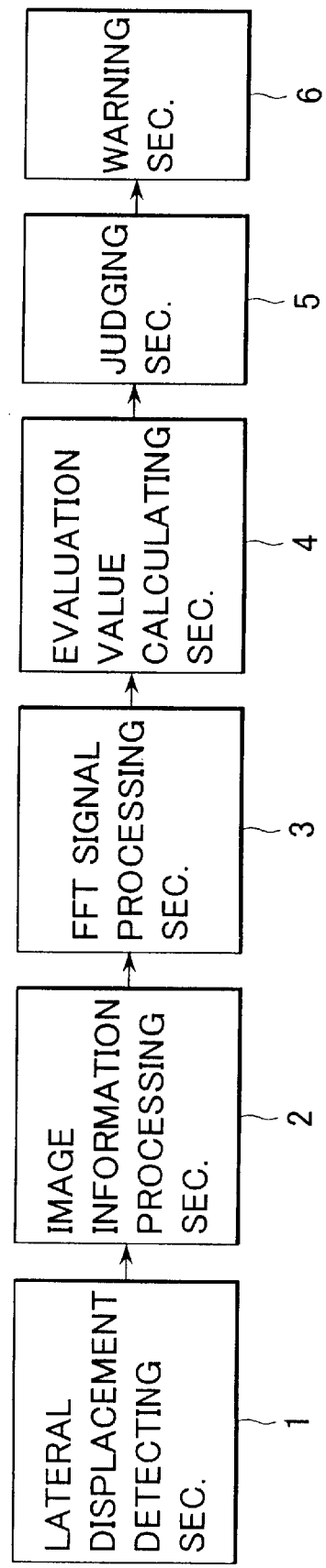
FIG. 1 is a block diagram showing an arousal level estimating apparatus according to the present invention.

Referring now to FIG. 1, reference numeral 1 denotes a lateral displacement detecting section for detecting a displacement in a widthwise direction of the vehicle (hereinafter referred to as lateral displacement). For the purpose of the lateral displacement detecting section 1, for example, a stereoscopic camera using CCD and the like or a monocular camera can be used. An image information processing section 2 serves as processing images acquired by the lateral displacement detecting section 1 and obtaining quantities of displacement of the vehicle. For example, left and right lane markers of roads are imaged by a CCD camera and image data of one frame are stored in a memory of the image information processing section 2. Then, the left and right lane markers are recognized respectively by utilizing image recognition technique. That is, an area corresponding to the left and right lane markers is identified from the image data of one frame using known methods of recognition like a template method or stereomatching method. The position of the own vehicle within the left and right lane markers can be calculated from the lateral distance from a center of the vehicle to a center of the left and right lane markers.

Besides the CCD camera, lateral displacement can be detected also by a vehicle-road communication system using magnetic nails buried in roads, a GPS navigation system combined with vehicle speeds and the like (regarding a technique of warning using a navigation system, see Japanese Patent Application Laid-open No. Toku-Kai-Hei 9-99756). Also, lateral displacement can be estimated by steering angles and the lateral displacement detecting section 1 can be replaced with a steering angle sensor. Furthermore, lateral displacement may be estimated by detecting yaw rate or lateral acceleration. Fluctuations or displacement quantities in the lateral direction of the vehicle are measured with resolution of 1.0 millimeter at a time interval of 0.1 seconds. Displacement related data is stored in a shift register of a FFT signal processing section 3 for obtaining frequency components power. A group of displacement data calculated in time series and accumulated for a specified time are stored. These data are updated successively by newly calculated data.

The FFT signal processing section 3, an evaluation value calculating section 4 and a judging section 5 are constituted by CPU, RAM, ROM and input and output circuits respectively and act as functional units in the computer. These functional units 3 to 5 are realized when respective components of the computer operate on each other under the control of an application program for executing a routine which will be described hereinafter. In the ROM, programs, a lower limit value PLOW, a table for establishing a step value a, warning judging values D1, D2 and the like are stored.

Figure 2:
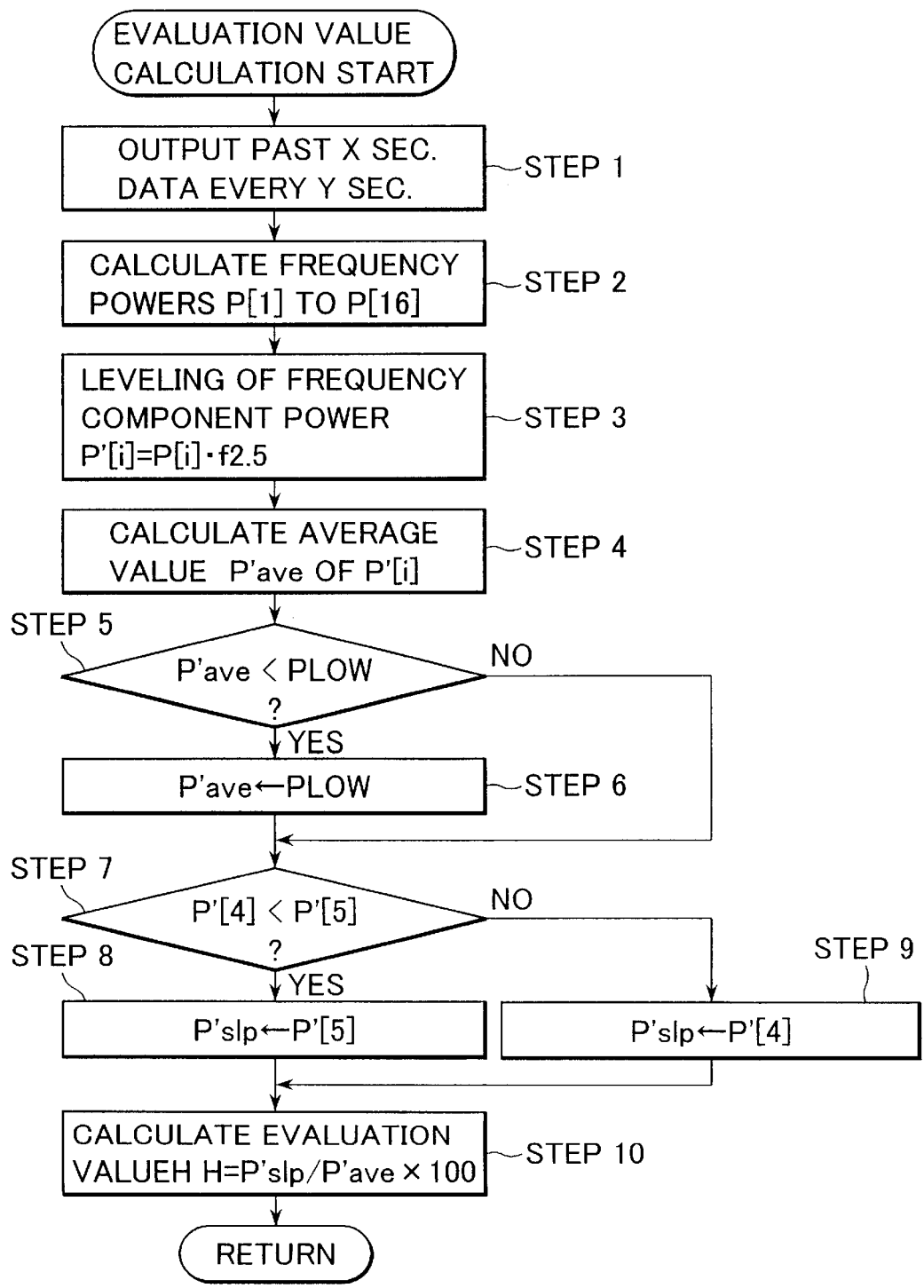
FIG. 2 is a flowchart of a routine for calculating evaluation values.

FIG. 2 is a flowchart of a routine for calculating evaluation values. This routine is executed repeatedly at a specified time interval. At a step 1, the displacement data acquired for the past X seconds and stored in the shift register of the FFT signal processing section 3 are read out every Y seconds (for example, 90 seconds). The sampling time X should be established at a rather long time (for example 50 to 80 seconds) in order to make an accurate estimation of arousal level.

At a step 2, the FFT signal processing section 3 applies a frequency conversion to the displacement quantity using a fast Fourier transformation (FFT) and the like and calculates respective frequency components power (amplitude) P[i] in a frequency spectrum. In case of this embodiment, 16 frequency components powers P[1] to P[16] are calculated at an interval of 0.02 [Hz] in a frequency domain of 0.03 to 0.3 [Hz]. The reason why the frequency domain below 0.03 Hz is not taken into consideration is that powers of that domain tend to increase when the vehicle travels on a curved road and the frequency domain has no direct relationship with driver's arousal level. Further, the reason why the frequency domain above 0.3 Hz is not taken into consideration is that since normally powers are negligibly small at that frequency domain, the amount of calculation of evaluation value H can be reduced.

Figure 3:
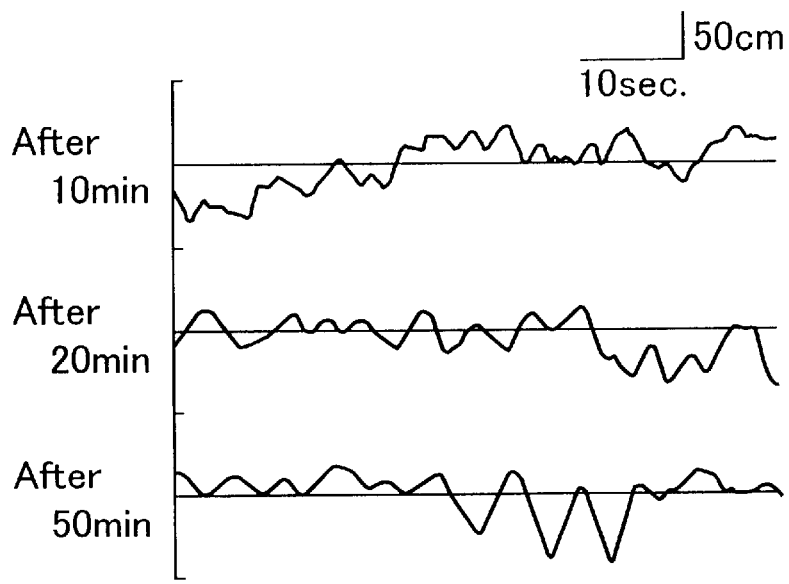
FIG. 3 is a diagram showing a time-versus change of lateral displacement.

The relationship between displacement quantity and frequency component power will be described. FIG. 3 is graphs showing the relationship between the change of lateral displacement quantity and elapsed time from the start of a vehicle. These graphs show the result of measurement when the vehicle travels on a relatively less crowded high way under a relatively monotonous traveling condition. The graph "After 10 minutes" shows a state immediately after the vehicle enters into the traffic stream and the displacement quantity is still small. When 20 minutes elapses, a driver gets accustomed to the traveling condition and becomes relaxed. As a result, compared with the graph "After 10 minutes", low frequency components increases and high frequency components decreases. Further, when 50 minutes elapses, the driver is bored and becomes slightly dozy. As a result, occasionally, a large displacement tends to generate. Compared with the graph "After 20 minutes", there is an outstanding tendency that the displacement quantity of low frequency components increases.

Figure 4:
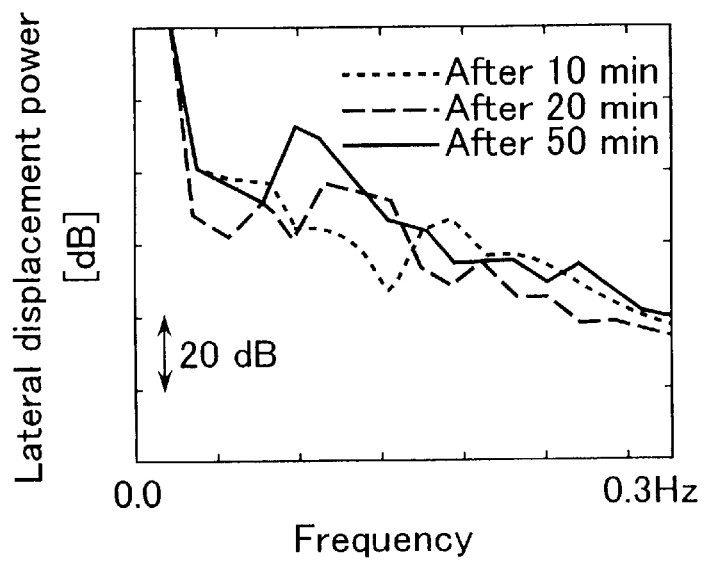
FIG. 4 is a graph showing respective powers of frequency components.

FIG. 4 is a graph showing a relationship between a frequency component i and a power P[i] at the frequency component I, when the displacement quantity for each elapsed time of FIG. 3 is subjected to frequency conversion and a graph expressing discrete respective frequency component powers P[i] as broken line. In this graph, a dotted line shows frequency component powers P[i] when 10 minutes elapse after the start of the vehicle, a broken line shows frequency component powers P[i] when 20 minutes elapse after the start of the vehicle, and a solid line shows frequency powers P[i] when 50 minute elapse after the start of the vehicle. The graph indicates that frequency component powers P[i] of the low frequency domain has a tendency to increase as traveling time is elongated.

At a step 3, respective frequency component powers P[i] (i=1 to 16) in a frequency domain of 0.03 to 0.3 [Hz] are subjected to a leveling process according to the following formula to obtain leveled frequency component powers P'[i].

$$P'[i]=P[i] \cdot f^n$$ [Formula 1]

where exponent n: 2.0 n 3.0; f=frequency.

Assuming that the fluctuation of the vehicle within a lane is one of various fluctuations existing in the natural world, the amplitude of the fluctuation is $1/f$ and the power of the fluctuation is $1/f^2$. Accordingly, the exponent n of the formula 1 is theoretically 2. However, according to experiments, it has been found that n=2.5 is most preferable. The reason why n=2.5 is considered to be ascribed to vehicle and human factors, the effect of roads or the like. Nevertheless, it is possible to judge an arousal level using an arbitrary exponent n ranging from 2.0 to 3.0. This embodiment adopts 2.5 for exponent n.

Figure 5:
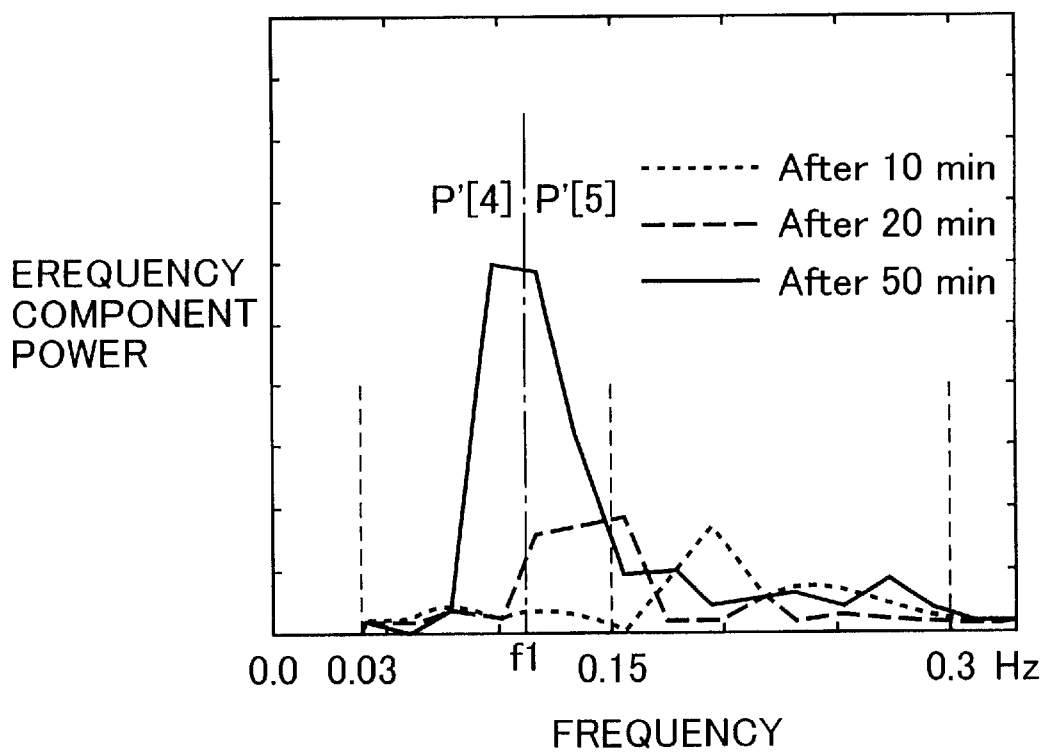
FIG. 5 is an explanatory view showing calculations of evaluation values.

FIG. 5 shows a relationship between frequency components i and leveled frequency component powers P'[i]. An overall feature can be visually recognized from a distribution of the leveled frequency powers P'[i]. The frequency component power after 50 minutes indicates that a power P'[4] at 0.09 Hz and a power P'[5] at 0.11 Hz of a low frequency domain abruptly increase in vicinity of a fluctuation frequency f1(=0.1 Hz). When driver's arousal level is at a low level, there is a tendency that with respect to lateral displacement of the vehicle the powers near the fluctuation frequency f1 increase. In other words, when an arousal level is low, there is a feature that only powers in a low frequency domain including the fluctuation frequency f1 increases and powers except that domain are low. In view of these tendencies, driver's arousal level can be judged by comparing a peak of powers near the fluctuation frequency f1 with powers at frequency domains other than the fluctuation frequency f1.

The fluctuation frequency f1 is defined as a frequency which increases when driver's arousal level is low (including a dozing condition). Generally, in case of passenger cars, the fluctuation frequency tends to appear at at a frequency domain around 0.08 to 0.12 Hz. In actual cases, since the fluctuation frequency is affected by a response lag of vehicle behavior accompanied by steering operations, vehicle characteristics, vehicle speeds and the like, appropriate values are established for each model through experiments or simulations. In this embodiment, the fluctuation frequency f1 is established to 0.1 Hz.

At a step 4, the evaluation value calculating section 4 obtains a grand total of respective frequency component powers P'[1] to P'[16] and calculates an average value P'$_{ave}$. According to the embodiment, in order to correctly reflect driver's arousal level on an evaluation value H which will be described hereinafter, a maximum power being excluded from the frequency powers P'[1] to P'[16], the average value P'$_{ave}$ is calculated from the rest of frequency powers P'[1] to P'[16]. The reason why thus filtering is performed is that the effect of increasing power of the fluctuation frequency f1 and the effect of disturbances are deleted.

At a step 5, the evaluation value calculating section 4 judges whether or not the average value P'$_{ave}$ is smaller than a lower limit value PLOW (for example 100) established beforehand. In case where the average value P'$_{ave}$ is smaller than the lower limit value PLOW, the arousal condition of the driver is judged to be stable and the lower limit value PLOW is set to the average value P'$_{ave}$ (step 6). This is for preventing the evaluation value H from growing unreasonably large when the evaluation value H is calculated at a step 10. On the other hand, in case where the average value P'$_{ave}$ is larger than the lower limit value PLOW, the program skips to a step 7.

At the step 7, the evaluation value calculating section 4 makes a comparison of sizes between frequency component powers P'[4] and P'[5] in a specified frequency domain (0.09 to 0.11 Hz). That frequency domain includes a fluctuation frequency f1 (0.01 Hz). Then, a larger one is set as a fluctuation frequency power P'$_{slp}$. That is, in case where the power P'[5] at 0.11 Hz is larger than the power P'[4] at 0.09 Hz, the power P'[5] is set to the fluctuation frequency power P'$_{slp}$ (step 8). On the other hand, in case where the power P'[5] at 0.11 Hz is smaller than the power P'[4] at 0.09 Hz, the power P'[4] is set to the fluctuation frequency power P'$_{slp}$ (step 9).

At a step 10, the evaluation value calculating section 4 calculates an evaluation value H according to the following formula:

$$H = P'_{slp} / P'_{ave} \times 100 \qquad \text{[Formula 2]}$$

This evaluation value is considered to be a momentary arousal level not including a time factor and is calculated as a ratio of the maximum power P'$_{slp}$ at the frequency domain 0.09 to 0.11 Hz to the average value P'$_{ave}$ of respective frequency component powers P'[i]. After the evaluation value H is calculated at the step 10, the program leaves the routine. As shown in FIG. 5, when 10 minutes elapse, since the power P'$_{slp}$ (P'[4] or P'[5]) is small, the evaluation value H is also small. On the other hand, when 50 minutes elapse, a driver's arousal level goes down. As a result, the power P'$_{slp}$ increases and the evaluation value H becomes large. Thus, it is understood that the evaluation value H has a strong correlation with the driver's arousal level.

Figure 6:
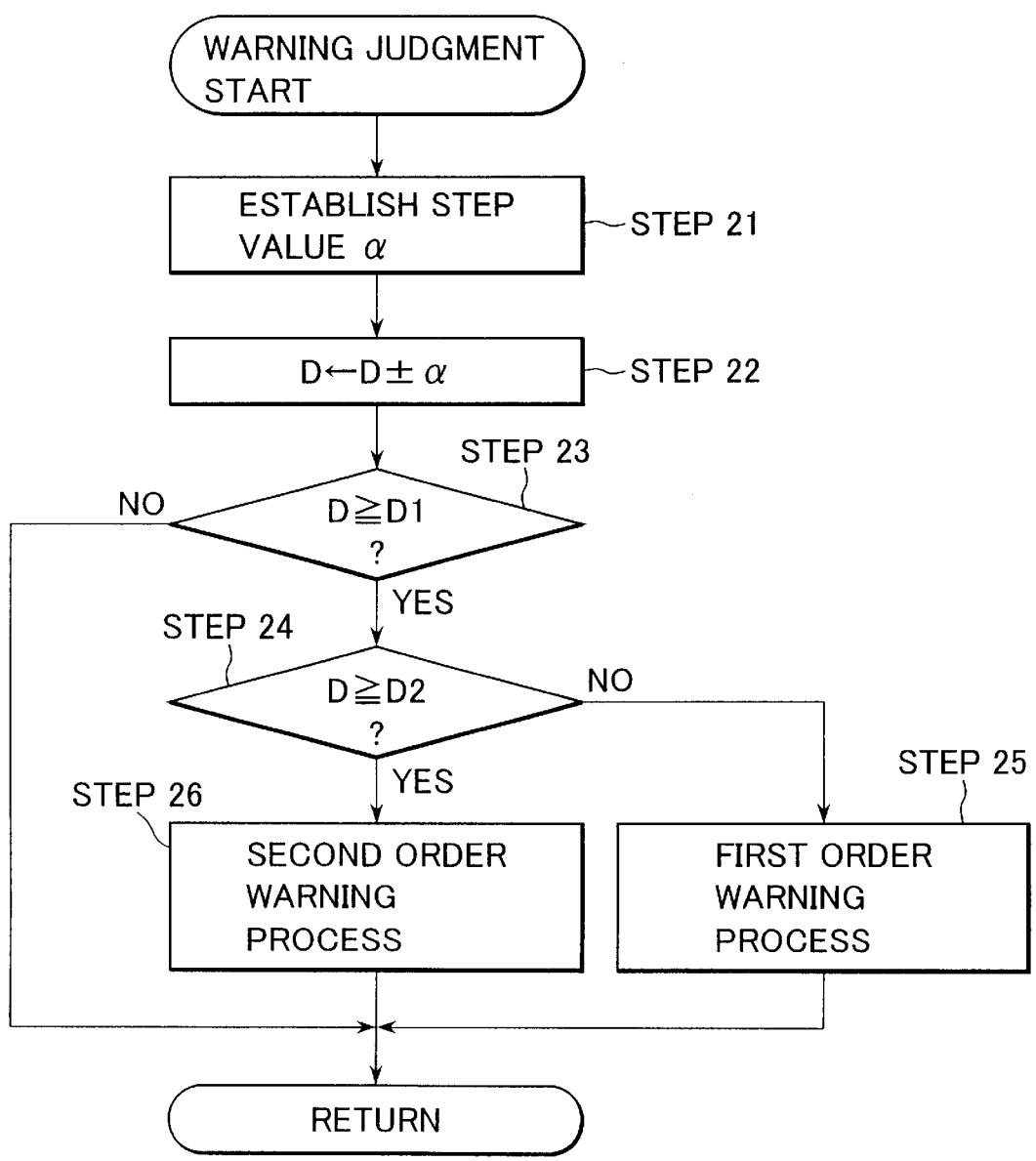
FIG. 6 is a flowchart of a routine for judging warning.

FIG. 6 is a flowchart of a routine for judging warnings. This routine is repeatedly executed at a specified interval. First, at a step 21, the judging section 5 establishes constants α1 to α8, 0 as step values according to the following table based on an evaluation value H calculated in the evaluation value calculating routine. These constants are for varying a value of an arousal level counter D and has a nonlinear relationship like |α1|>|α2|>|α3|>|α4|>|α5|,|α6|<|α7|<|α8|. (Establishment of Step Values

| Evaluation value | Step value |
|---|---|
| >1000 | +α1 |
| >900 | +α2 |
| >800 | +α3 |
| >500 | +α4 |
| >400 | +α5 |
| >300 | ±0 |
| >200 | −α6 |
| >100 | −α7 |
| >0 | −α8 |

Next, at a step 22, the judging section 5 updates the value of the arousal level counter D by adding or subtracting a step value a to or from the present value of the arousal level counter D. Then, at a step 23, it is judged whether or not the updated value of the arousal level counter D is larger than a first judging value D1 (1$^{st}$ warning judgment). If the updated value of the arousal level counter D is smaller than the first judging value D1, it is judged that the driver is in an arousal state and the program leaves the routine. On the other hand, if the updated value of the arousal level counter D is larger than the first judging value D1, the program goes to a step 24.

At the step 24, it is judged whether or not the value of the arousal level counter D is larger than a second judging value D2 (2$^{nd}$ warning judgment). If the value of the arousal level counter D is smaller than the second judging value D2, the program goes to a step 25 where, in order to warn fluctuations of the vehicle, it is instructed to the warning section 6 that a first warning should be issued and leaves the routine. On the other hand, if the value of the arousal level counter D is larger than the second judging value D2, the program goes to a step 26, where in order to warn the driver in a dozing state, it is instructed to the warning section 6 that a second warning should be issued and leaves the routine.

The earning section 6 executes miscellaneous warning processes to urge the driver to wake up responding to the instruction from the judging section 5. There is a variety of warning processes. One example is to sound an alarm. In case where it is judged that the arousal level descends, an reference inter-vehicle distance may be established to a rather long value. The warning section 6 may sounds a lane running-off alarm in a rather early timing or sounds a dozing alarm directly. Further, when the arousal level descends, the warning section 6 may instruct to display "Car fluctuates" on a dashboard of the vehicle.

FIG. 7 is a graph showing an actual measurement result when a vehicle travels at high speeds. In which, a lower diagram indicates a characteristic of lateral displacement of a vehicle, upper one indicates a characteristic of evaluation values H and a middle one indicates a characteristic of the arousal level counter D, respectively. According to this measurement result, when around 1400 seconds elapse from the start of the vehicle, peaks characteristic of lateral displacement appear successively and the fluctuation frequency f1 (=0.1 Hz) is found. As a result, the evaluation value H increases and the value of the deviation counter D is incremented. When this increment occurs successively, an alarm is raised to the driver at an appropriate timing. According to the characteristic of lateral displacement of FIG. 7, the peaks appear before 1400 seconds. However, according to the embodiment, unless such peaks appear successively (unless the arousal level counter D is successively incremented), the warning section 6 does not raise a warning.

Thus, according to the embodiment, the driver's arousal level is judged by comparing the peaks of powers around the fluctuation frequency f1 with the powers of other frequency domains. Therefore, the driver's arousal level can be judged only on the basis of the present and previous data. As a result, the arousal level can be properly judged even if the traveling condition changes.

In calculating the evaluation value H, with respect to the average value P'$_{ave}$ of the frequency powers P'[I], since the lower limit value is established in order to prevent the denominator of the formula 2 from becoming excessively small, the arousal level can be estimated accurately without having adverse effects of small disturbances when the vehicle travels at high speeds and driving patterns inherent to individual drivers.

Further, in this embodiment, when peaks of powers in the frequency domain including the fluctuation frequency f1 stand out against powers of other frequency domains, the lowered arousal level is detected. This method provides an advantage of preventing erroneous judgments of the arousal level even when lateral displacement quantity is small, or even when the vehicle has a light side wind or even when a large vehicle passes by.

Further, according to a prior art, a final arousal level is calculated from a time average of sporadic arousal levels and the judgment of warning is made by comparing this final arousal level is compared with a threshold value. However, this method according to the prior art has a problem that the warning is accompanied by time lag. On the other hand, according to the method of the present invention, in case where an evaluation value H corresponding to sporadic arousal levels is large (particularly in case where the arousal level is substantially low), the step value α of the arousal level counter D is established to a large value. Accordingly, the warning can be issued without time lag.

While the present invention has been disclosed in terms of the preferred embodiment in order to facilitate better understanding of the invention, it should be appreciated that the invention can be embodied in various ways without departing from the principle of the invention. Therefore, the invention should be understood to include all possible embodiments which can be embodied without departing from the principle of the invention set out in the appended claims.

What is claimed is:

1. An arousal level estimating apparatus for estimating an arousal level of a driver of a vehicle comprising:
    a power calculating means for calculating a frequency component power by applying a frequency conversion method to a lateral displacement quantity detected successively;
    a first evaluation value calculating means for calculating a first evaluation value based on a sum of said frequency component power calculated by said power calculating means;
    a second evaluation value calculating means for calculating a maximum value of frequency component power in a specified frequency domain including a fluctuation frequency as a second evaluation value;
    an evaluation value calculating means for calculating an evaluation value from a ratio of said first evaluation value and said second evaluation value; and
    a judging means for judging a driver's arousal level based on said evaluation value.

2. The apparatus according to claim 1, wherein said frequency component powers are subjected to a leveling process.

3. The apparatus according to claim 2, wherein said leveled frequency component power is obtained by multiplying said frequency component power by a frequency raised to n power.

4. The apparatus according to claim 3, wherein said exponent n is a value not more than 3 and not less than 2.

5. The apparatus according to claim 1, wherein said first evaluation value is obtained based on said frequency component powers excluding a maximum one from said respective frequency component powers calculated by said power calculating means.

6. The apparatus according to claim 1, wherein said evaluation calculating means calculates said evaluation value in time sequence and said judging means increases or decreases a counter value according to said evaluation value and when said counter value reaches a judging value, judges that a warning should be raised to a driver of said vehicle.

7. The apparatus according to claim 6, wherein said judging means changes said counter value according to said evaluation value.

8. An arousal level estimating method, comprising:
    calculating a frequency component power by applying a frequency conversion method to a lateral displacement quantity detected successively;
    calculating a first evaluation value based on a sum of said frequency component power;
    calculating a maximum value of frequency component power in a specified frequency domain including a fluctuation frequency as a second evaluation value;
    calculating an evaluation value from a ratio of said first evaluation value and said second evaluation value; and
    judging a driver's arousal level based on said evaluation value.

9. The method according to claim 8, wherein said calculating said first evaluation value obtains said first evaluation value based on said frequency component powers excluding a maximum one from said respective frequency component powers calculated by said calculating said frequency component power.

10. The method according to claim 8, wherein said calculating said evaluation value comprises calculating said evaluation value in time sequence.

11. The apparatus according to claim 1, wherein said power calculating means comprises a fast Fourier transformation section applying a fast Fourier transformation to calculate said frequency component power.

12. The apparatus of claim 1, wherein said power calculating means subjects a range of said frequency component power to a leveling process defined as $$P'[i]=P[i]*f^n$$

wherein 2.0<n<3.0 and f is equal to a frequency, to determine leveled frequency component powers P'[i].

13. The method according to claim 8, wherein said judging comprises one of increasing and decreasing a counter value according to said evaluation value, and, when said counter value reaches a judging value, comprises judging that a warning should be raised to a driver of said vehicle.

14. The method according to claim 8, further comprising: subjecting said frequency component power to a leveling process.

15. The method according to claim 8, wherein said calculating a frequency component power comprises applying a fast Fourier transformation to calculate said frequency component power.

16. A computer-readable medium having computer-executable instructions for performing an estimation of an arousal level of a driver of a vehicle, comprising:
    calculating a frequency component power by applying a frequency conversion method to a lateral displacement quantity detected successively;
    calculating a first evaluation value based on a sum of said frequency component power;
    calculating a maximum value of frequency component power in a specified frequency domain including a fluctuation frequency as a second evaluation value;
    calculating an evaluation value from a ratio of said first evaluation value and said second evaluation value; and judging a driver's arousal level based on said evaluation value.

17. The computer-readable medium of claim 16, wherein said calculating said evaluation value comprises calculating said evaluation value in time sequence.

18. The computer-readable medium of claim 16, wherein said judging comprises increasing or decreasing a counter value according to said evaluation value.

19. The computer-readable medium of claim 18, wherein said judging comprises, when said counter value reaches a judging value, judging that a warning should be raised to a driver of said vehicle.

20. The computer-readable medium of claim 16, wherein said frequency component power is subjected to a leveling process.

21. An arousal level estimating system for estimating an arousal level of a driver of a vehicle, comprising:

a power calculator for calculating a frequency component power by applying a frequency conversion method to a lateral displacement quantity detected successively;

a first evaluation calculator for calculating a first evaluation value based on a sum of said frequency component power calculated by said power calculating means;

a second evaluation value calculator for calculating a maximum value of frequency component power in a specified frequency domain including a fluctuation frequency as a second evaluation value;

an evaluation value calculator for calculating an evaluation value from a ratio of said first evaluation value and said second evaluation value; and a judging section for judging a driver's arousal level based on said evaluation value.

22. The system of claim 21, wherein, wherein said evaluation value calculator calculates said evaluation value in time sequence.

23. The system of claim 21, wherein said power calculator comprises a fast Fourier transformation section applying a fast Fourier transformation to calculate said frequency component power.

24. The system of claim 21, wherein said power calculator subjects a range of said frequency component power to a leveling process defined as $$P'[i]=P[i]*f_n$$

wherein $2.0<n<3.0$ and f is equal to a frequency, to determine leveled frequency component powers $P'[i]$.

25. The system of claim 21, wherein said judging section increases or decreases a counter value according to said evaluation value, and, when said counter value reaches a judging value, judges that a warning should be raised to a driver of said vehicle.

* * * * *